United States Patent
Ye

(10) Patent No.: US 9,670,156 B2
(45) Date of Patent: Jun. 6, 2017

(54) CRYSTAL FORM III OF (S)-OXIRACETAM, PREPARATION METHOD AND USE THEREOF

(71) Applicant: Chongqing Runze Pharmaceutical Company Limited, Chongqing (CN)

(72) Inventor: Lei Ye, Chongqing (CN)

(73) Assignee: Chongqing Ruzer Pharmaceutical Company Limited (CN)

( * ) Notice: Subject to any disclaimer, the term of this patent is extended or adjusted under 35 U.S.C. 154(b) by 0 days.

(21) Appl. No.: 15/122,567

(22) PCT Filed: Oct. 27, 2014

(86) PCT No.: PCT/CN2014/089527
§ 371 (c)(1),
(2) Date: Oct. 4, 2016

(87) PCT Pub. No.: WO2015/067130
PCT Pub. Date: May 14, 2015

(65) Prior Publication Data
US 2017/0073307 A1    Mar. 16, 2017

(30) Foreign Application Priority Data
Nov. 6, 2013  (CN) .......................... 2013 1 0544812

(51) Int. Cl.
*C07D 207/273*   (2006.01)
*A61K 31/4015*   (2006.01)

(52) U.S. Cl.
CPC ...... *C07D 207/273* (2013.01); *C07B 2200/13* (2013.01)

(58) Field of Classification Search
None
See application file for complete search history.

(56) References Cited

U.S. PATENT DOCUMENTS

| 9,126,929 B2 | 9/2015 | Ye |
| 2007/0185337 A1 | 8/2007 | Kim et al. |
| 2013/0059900 A1 | 3/2013 | You et al. |
| 2014/0171659 A1 | 6/2014 | Ye et al. |
| 2014/0303383 A1 | 10/2014 | Ye et al. |

FOREIGN PATENT DOCUMENTS

| CN | 1956953 A | 5/2007 |
| CN | 101121688 A | 2/2008 |
| CN | 101367757 A | 2/2009 |
| CN | 101575309 A | 11/2009 |
| CN | 102050774 A | 5/2011 |
| CN | 102101836 A | 6/2011 |
| CN | 102249975 A | 11/2011 |
| CN | 102351770 A | 2/2012 |
| CN | 102452972 A | 5/2012 |
| CN | 102531988 A | 7/2012 |
| CN | 102531989 A | 7/2012 |
| CN | 102558013 A | 7/2012 |
| CN | 102558014 A | 7/2012 |
| CN | 102603594 A | 7/2012 |
| CN | 102603595 A | 7/2012 |
| CN | 102603596 A | 7/2012 |
| CN | 102603597 A | 7/2012 |
| CN | 102617437 A | 8/2012 |
| CN | 103553997 A | 2/2014 |
| CN | 103553998 A | 2/2014 |
| CN | 103553999 A | 2/2014 |
| CN | 103554000 A | 2/2014 |
| WO | WO-93/06826 A1 | 4/1993 |
| WO | WO-2013020391 A1 | 2/2013 |

OTHER PUBLICATIONS

CN102101836A (published Jun. 22, 2011; English translation, machine).*

* cited by examiner

*Primary Examiner* — Michael Barker
(74) *Attorney, Agent, or Firm* — Blank Rome LLP

(57) ABSTRACT

(S)-4-hydroxy-2-oxo-1-pyrrolidine crystal form III (called crystal form III of (S) -oxiracetam for short) has diffraction peaks at diffraction angles 2θ, wherein the diffraction angles 2θ are equal to 10.54, 13.70, 14.44, 15.60, 17.12, 18.88, 19.24, 20.66, 20.84, 21.18, 21.82, 22.94, 23.24, 24.88, 27.20, 27.48, 28.24, 30.46, 30.80, 31.52, 32.00, 32.34, 32.90, 33.20, 34.40, 34.62, 37.30, 37.50, 38.28, 38.96, and 40.02°. The (S)-oxiracetam crystal form III of the present invention has an obvious effect on memory dysfunction, is dissolved in water fast, has high bioavailability, and can be used to prepare various pharmaceutical compositions. The (S)-oxiracetam crystal form III obtained by using the preparation method of the present invention is high in purity. The preparation method of the present invention is performed in a mild condition, is easy in operation, introduces less impurities, has desirable reproducibility, is easily controlled during production, and is applicable to industrial production.

20 Claims, 3 Drawing Sheets

CRYSTAL FORM III OF (S)-OXIRACETAM, PREPARATION METHOD AND USE THEREOF

RELATED APPLICATIONS

The present application is a National Phase of PCT Patent Application PCT/CN2014/089527 filed Oct. 27, 2014, which claims priority to Chinese Patent Application No. 201310544812.8 filed Nov. 6, 2013. The entire disclosures of those applications are hereby incorporated by reference.

FIELD OF THE INVENTION

The present invention relates to the field of medicine, particularly relates to oxiracetam, and more particularly relates to a new crystal form of (S)-oxiracetam, preparation method, and use thereof.

DESCRIPTION OF THE PRIOR ART

Oxiracetam, CAS No. 62613-82-5, is a new generation of medicines to improve cerebral metabolism, and it is a derivative of pyrrolidones (cyclic GABOB), an analogue of piracetam. Oxiracetam can promote the synthesis of phosphoryl choline and phosphoryl ethanolamine, and it promotes cerebral metabolism. It shows stimulatory effects to specific central nervous pathway through blood-brain barrier, and improves intelligence and memory. Oxiracetam has good effect on cerebrovascular diseases, brain damages, brain tumors (after surgery), intracranial infections, dementia, and degenerative brain diseases. It is suitable for impediment of anamnesis and aptitude caused by mild to moderate vascular dementia, senile dementia and traumatic brain injury etc. Oxiracetam was firstly synthesized by Italy Smith Kline Beecham Ltd in 1974 and came into the market in 1987 in Italy. It is better than piracetam to focus the memory especially the thinking, and less toxic. A report shows that (S)-oxiracetam has higher activity than (R)-oxiracetam.

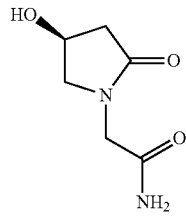

CN 102050774A reports a refining method for oxiracetam compound; CN 101121688A discloses an improved process for oxiracetam; CN 101575309A, CN 101367757, and CN 101575309 disclose a process for synthesizing (S)-oxiracetam, respectively. CN 102249975 A discloses the crystal form I of (S)-oxiracetam and the preparation method thereof. CN 102351770 B discloses the dihydrate crystal form of oxiracetam. WO 2013/020391 A1 discloses the crystal form II of S-oxiracetam and the preparation method thereof.

The inventors found, through systematic polymorph screening experiments, that there are other crystal forms of (S)-oxiracetam, in addition to the already disclosed crystal form I and crystal form II. The crystal form I mentioned in the present invention refers to the crystal form in "Crystal form I of (S)-4-hydroxy-2-oxo-1-pyrrolidine acetamide and preparation method and use thereof" disclosed in Chinese Patent CN 102249975 A. The crystal form II refers to the crystal form disclosed in "Crystal form II of (S)-4-hydroxy-2-oxo-1-pyrrolidine acetamide and preparation method thereof" disclosed in Chinese Patent CN 102558013 A.

For polymorphs of medicines, different polymorphs may have different characteristics, such as chemical stability, melting point, apparent solubility, dissolution rate and density etc. These properties can directly affect the processing and production of the active pharmaceutical ingredients and the formulations, and will affect the stability, solubility and bioavailability of the formulations. In solid pharmaceutical formulations made from polymorphs, the solubility has direct impact on the bioavailability; and generally, the bioavailability is higher if the medicine has higher solubility. Thus, the polymorphs of medicines have important significance to the quality, safety and efficacy of pharmaceutical preparations.

SUMMARY OF THE INVENTION

The present invention provides a new crystal form of (S)-oxiracetam, which has other unique properties with respect to other solid forms of (S)-oxiracetam. Complete features of the present invention are described below, and the new crystal form of (S)-oxiracetam is referred to as "crystal form III" for convenience.

One object of the present invention is to provide a new crystal form III of (S)-oxiracetam, and apply it to the pharmaceutical composition formulations.

Another object of the present invention is to provide a preparation method for the above new crystal form III of (S)-oxiracetam.

A further object of the present invention is to provide the use of the above new crystal form III of (S)-oxiracetam in medicines.

The objects of the present invention are implemented as follows:

The new crystal form III of (S)-oxiracetam has diffraction peaks appearing at the following 2θ diffraction angles: 14.44, 17.12, 18.88, 19.24, 20.66, 20.84, and 21.18°.

Specifically, the new crystal form III of (S)-oxiracetam has diffraction peaks appearing at the following 2θ diffraction angles: 10.54, 13.70, 14.44, 15.60, 17.12, 18.88, 19.24, 20.66, 20.84, 21.18, 21.82, 22.94, 23.24, 24.88, 27.20, 27.48, 28.24, 30.46, 30.80, 31.52, 32.00, 32.34, 32.90, 33.20, 34.40, 34.62, 37.30, 37.50, 38.28, 38.96, and 40.02°.

The above crystal form III of (S)-oxiracetam has an X-ray powder diffraction data expressed in terms of d (Å)-values and relative intensity percentages I (%) as shown below:

| d value | I value | d value | I value |
| --- | --- | --- | --- |
| 8.3851 | 6.0 | 6.4588 | 8.5 |
| 6.1284 | 24.8 | 5.6744 | 10.0 |
| 5.1759 | 50.5 | 4.6969 | 100.0 |
| 4.6099 | 46.3 | 4.2960 | 34.2 |
| 4.2590 | 25.9 | 4.1914 | 71.1 |
| 4.0697 | 33.0 | 3.8735 | 33.8 |
| 3.8242 | 17.0 | 3.5761 | 67.5 |
| 3.2758 | 8.9 | 3.2429 | 7.9 |
| 3.1575 | 10.9 | 2.9324 | 19.8 |
| 2.9006 | 8.5 | 2.8362 | 23.2 |
| 2.7944 | 5.4 | 2.7661 | 23.9 |
| 2.6047 | 5.4 | 2.5888 | 16.8 |
| 2.4088 | 7.5 | 2.3963 | 10.6 |
| 2.3492 | 5.0 | 2.3097 | 16.9 |
| 2.2510 | 6.4. | | |

The unit cell of the above crystal form III of (S)-oxiracetam is orthorhombic, space group is $P4_1$, a=6.583 Å, b=6.583, and has a crystal structure as shown in FIG. 1.

The infrared spectrum produced from the above new crystal form III of (S)-oxiracetam shows absorption peaks at the following wave numbers:

3402($cm^{-1}$), 3356($cm^{-1}$), 3186($cm^{-1}$), 2927($cm^{-1}$), 2881 ($cm^{-1}$), 2810($cm^{-1}$), 1672($cm^{-1}$), 1491($cm^{-1}$), 1452($cm^{-1}$), 1398($cm^{-1}$), 1308($cm^{-1}$), 1240($cm^{-1}$), 1199($cm^{-1}$), 1082 ($cm^{-1}$), 1037($cm^{-1}$), 1012($cm^{-1}$), 947($cm^{-1}$), 671($cm^{-1}$), 613($cm^{-1}$), and 461($cm^{-1}$).

The peak value of the melting point of the above new crystal form III of (S)-oxiracetam is 117.3° C. This crystal form has a differential scanning calorimetry (DSC) thermogram as shown in FIG. 4.

The crystal form III of the present invention has the same chemical structure as (S)-oxiracetam. It also has activity of promoting the synthesis of phosphoryl choline and phosphoryl ethanolamine, promoting cerebral metabolism, having stimulatory effects to specific central nervous pathway through blood-brain barrier, and improving intelligence and memory. Its solubility in water is >100 mg/ml, and it has high bioavailability. Compared with other crystal forms of (S)-oxiracetam, the crystal form III of (S)-oxiracetam of the present invention dissolves fast in aqueous solution, which is especially suitable for the preparation of first aid medicine.

The above new crystal form III of (S)-oxiracetam is prepared by cooling crystallization or freeze-drying crystallization method.

The cooling crystallization method is as the following steps:
(1) Dissolving (S)-oxiracetam in an alcoholic solvent at 5 mg/ml-50 mg/ml, stirring constantly, heating to 30° C. to 100° C. to dissolve, and filtering to form a supersaturated solution; wherein the alcoholic solvent is one or more selected from n-propanol, isopropanol, and sec-butanol;
(2) Placing the supersaturated solution obtained in step (1) in a sealed low temperature environment at −10° C. to −19° C. for cooling crystallization, to give colorless blocky crystal, which is the new crystal form III of (S)-oxiracetam.

In the above step (2), the crystals begin to precipitate at about 3-4 hours, and reach equilibrium at 24-36 hours, then no more precipitation. The temperature of heating to dissolve is preferably at 40° C. to 50° C. The low temperature environment is preferably at −17° C. to −19° C.

Specifically, dissolving (S)-oxiracetam in n-propanol, isopropanol, or sec-butanol solvent at 5 mg/ml-50 mg/ml, stirring constantly, heating to 40° C. to 50° C. to dissolve, and filtering to form a supersaturated solution. Placing the solution in a sealed environment at −17° C. to −19° C. for cooling crystallization for 24-36 hours, to give colorless blocky crystal, which is the new crystal form III of (S)-oxiracetam.

The freeze-drying crystallization method is as the following steps:

Dissolving (S)-oxiracetam in water to form an aqueous solution at 10 mg/ml-20 mg/ml, placing in a refrigerator of −19° C. to freeze for 3 hours, then taking out into a refrigerator of −80° C. to pre-freeze for 8 hours, and then placing in a vacuum freeze dryer for freeze-drying for two days, to give the new crystal form III of (S)-oxiracetam.

The raw materials and reagents are all commercially available products.

A pharmaceutical composition, which comprises the above crystal form III of (S)-oxiracetam in a pharmaceutically acceptable excipient. The composition can be prepared in forms of tablets, powders, granules, capsules, injections, freeze-dried powders, pills, sustained release and controlled release formulations and so on, depending on different adaptations.

The use of the above crystal form III of (S)-oxiracetam in the manufacture of medicines for prevention or treatment of memory dysfunction is provided.

The beneficial effects of the invention are as follows:

The new crystal form III of (S)-oxiracetam of the present invention has the same advantages as oxiracetam: promoting the synthesis of phosphoryl choline and phosphoryl ethanolamine, promoting cerebral metabolism, having stimulatory effects to specific central nervous pathway through blood-brain barrier, improving intelligence and memory, and having significant effect on memory dysfunction. The peak value of the melting point of the new crystal form III of (S)-oxiracetam of the present invention is 117.3° C. Compared with other crystal forms of (S)-oxiracetam, the crystal form III of (S)-oxiracetam of the present invention dissolves fast in aqueous solution, which is especially suitable for the preparation of first aid medicine. Its solubility in water is ≥100 mg/ml. It has high bioavailability, and is suitable for preparation of a variety of pharmaceutical compositions. It can be prepared into a variety of formulations such as tablets, capsules, pills, sustained or controlled release formulations, freeze-drying powders and the like. The raw materials used in the preparation method of the present invention are cheap and can be easily obtained. The prepared (S)-oxiracetam crystal form III is high in purity. The preparation method is performed in a mild condition, and is easy in operation. It introduces less impurities, and has desirable reproducibility. It is easily controlled during production, and has high safety, and is applicable to industrial production.

DETAILED DESCRIPTION OF THE PREFERRED EMBODIMENTS

The present invention will be specifically described by the following examples. It is necessary to point out that the following examples are only for further describing the present invention, and cannot be construed as limiting the scope of the present invention. The skilled in the art can, according to the above description, make some unessential improvements and adjustments to the present invention.

Example 1

50 mg (S)-oxiracetam is dissolved in 2 ml n-propanol solution, heated to 40° C., and filtered to form a supersaturated solution. The supersaturated solution is placed in a sealed environment at −19° C. for cooling crystallization for 24 hours, to give a colorless blocky crystal, which is the crystal form III.

Example 2

The crystal parameters of the crystalline (S)-oxiracetam crystal form III obtained in Example 1 are measured.

Figure 1:
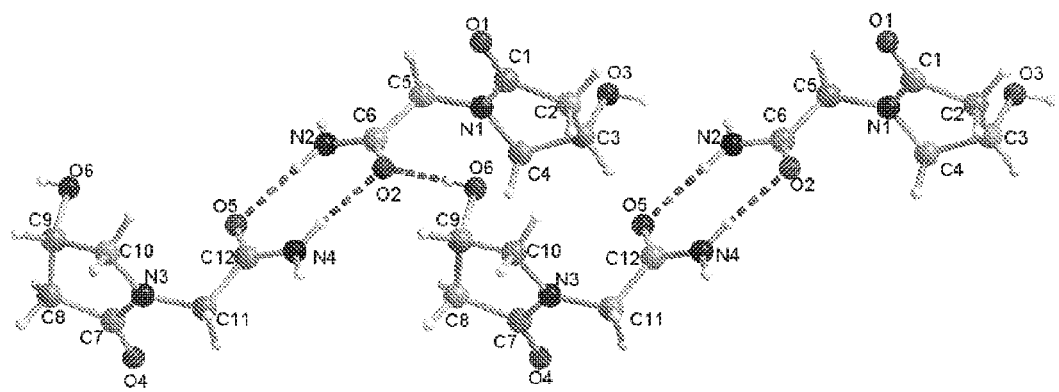
FIG. 1 is the crystal structure of the crystallized (S)-oxiracetam crystal form III.
Figure 2:
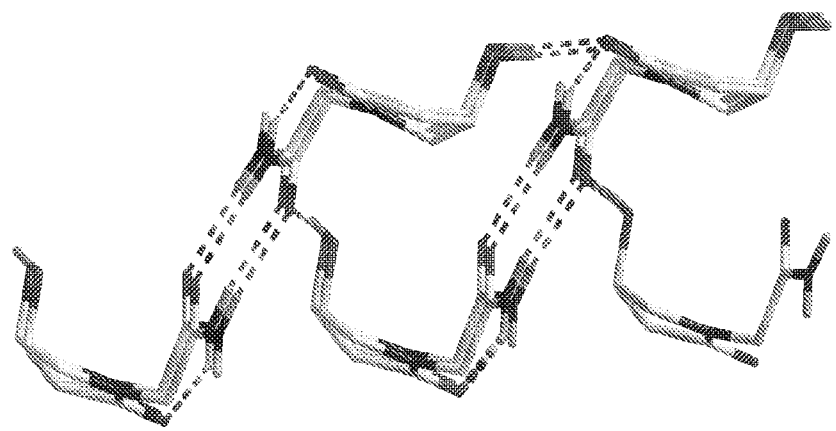
FIG. 2 is the crystal packing pattern of the crystallized (S)-oxiracetam crystal form III.

The single crystal structure of the crystal form III of (S)-oxiracetam is analyzed. The unit cell is orthorhombic, space group is $P4_1$, a=6.583 Å, b=6.583 Å, c=33.532(4) Å, α=90.00, β=90.00, γ=90.00, cell volume V=1453.059 (17) Å$^3$. The crystal structure is shown in FIG. 1, and the crystal packing is shown in FIG. 2.

The crystallography parameters of the crystalline (S)-oxiracetam crystal form III is shown in the following table:

|  | Crystal Form III |
|---|---|
| Molecular Formula | $C_6H_{10}N_2O_3$ |
| Molecular Weight | 158.16 |
| Space Group | $P4_1$ |
| Measurement temp./K | 150 (2) |
| a, Å | 6.583 |
| b, Å | 6.583 |
| c, Å | 33.5322 (4) |
| α, deg | 90 |
| β, deg | 90 |
| γ, deg | 90 |
| Z value | 8 |
| V, Å$^3$ | 1453.059 (17) |
| μ value/mm$^{-1}$ | 0.993 |
| Total diffraction points | 12935 |
| Number of diffraction points | 2741 |
| Independent reflection data//restraints/refinement parameter | 2741/1/211 |
| R indices [I > 2σ (I)] | 0.0439 |
| wR$_2$ [all data] | 0.1116 |
| Goodness of fit (GOOF) value | 1.070 |

$^a$R$_1$ = Σ | | F$_o$ | − | F$_c$ | |/Σ F$_o$ |.
$^b$wR$_2$ = [Σ[w(F$_o$$^2$ − F$_c$$^2$)$^2$]/Σw(F$_o$$^2$)$^2$]$^{1/2}$, w = 1/[σ$^2$ (F$_o$)$^2$ + (aP)$^2$ + bP], where P = [(F$_o$$^2$) + 2F$_c$$^2$]/3.

Figure 3:
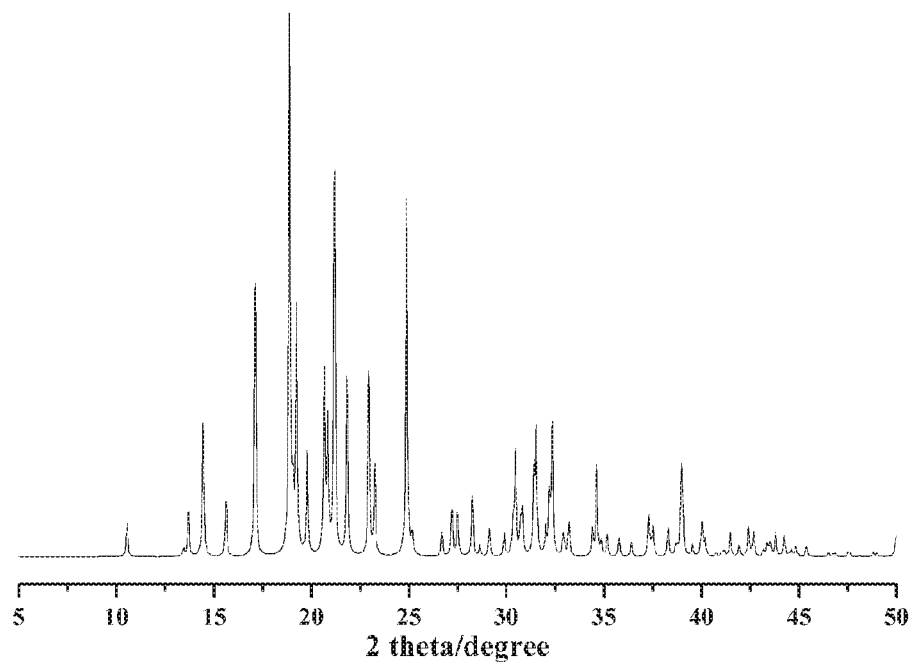
FIG. 3 is the X-ray powder diffraction pattern of the crystallized (S)-oxiracetam crystal form III, simulated from single crystal.
Figure 6:
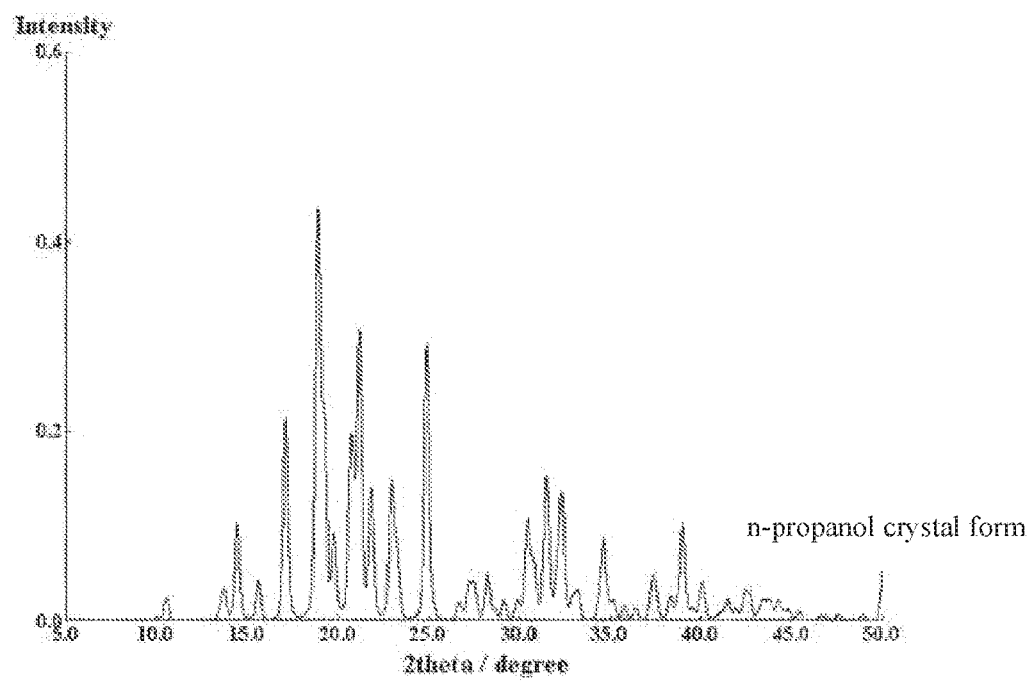
FIG. 6 is the single crystal X-ray powder diffraction pattern of the crystallized (S)-oxiracetam crystal form III.

The crystalline (S)-oxiracetam crystal form III has diffraction peaks appearing at the following 2θ diffraction angles: 10.54, 13.70, 14.44, 15.60, 17.12, 18.88, 19.24, 20.66, 20.84, 21.18, 21.82, 22.94, 23.24, 24.88, 27.20, 27.48, 28.24, 30.46, 30.80, 31.52, 32.00, 32.34, 32.90, 33.20, 34.40, 34.62, 37.30, 37.50, 38.28, 38.96, and 40.02 degrees. The X-ray powder diffraction pattern simulated from its single crystal is shown in FIG. 3, wherein the intensity peaks of the diffraction peaks are appearing at the following 2θ diffraction angles: 14.44, 17.12, 18.88, 19.24, 20.66, 20.84, and 21.18°. FIG. 3 is the powder diffraction pattern of the above crystalline (S)-oxiracetam simulated from the single crystal structure data. A single crystal simulation is simulated on the premise of perfect crystallization, while in practice, perfect crystallization is difficult to appear, which could lead to the merge of two adjacent peaks into one peak, thus resulting in peak broadening. The peaks in FIG. 6 coincide with those in FIG. 3, and the coincidence degree is more than 99%, which can be technically considered that the prepared crystalline (S)-oxiracetam crystal form III is a pure single crystal.

The X-ray powder diffraction pattern of the crystalline (S)-oxiracetam crystal form III of the present invention is expressed in terms of interplanar spacing d, Bragg angle (2θ) and relative intensity percentages I as shown below:

| 2θ degree | d/Å | Relative intensity I/% |
|---|---|---|
| 10.54 | 8.3851 | 6.0 |
| 13.70 | 6.4588 | 8.5 |
| 14.44 | 6.1284 | 24.8 |
| 15.60 | 5.6744 | 10.0 |
| 17.12 | 5.1759 | 50.5 |
| 18.88 | 4.6969 | 100.0 |
| 19.24 | 4.6099 | 46.3 |
| 20.66 | 4.2960 | 34.2 |
| 20.84 | 4.2590 | 25.9 |
| 21.18 | 4.1914 | 71.1 |
| 21.82 | 4.0697 | 33.0 |
| 22.94 | 3.8735 | 33.8 |
| 23.24 | 3.8242 | 17.0 |
| 24.88 | 3.5761 | 67.5 |
| 27.20 | 3.2758 | 8.9 |
| 27.48 | 3.2429 | 7.9 |
| 28.24 | 3.1575 | 10.9 |
| 30.46 | 2.9324 | 19.8 |
| 30.80 | 2.9006 | 8.5 |
| 31.52 | 2.8362 | 23.2 |
| 32.00 | 2.7944 | 5.4 |
| 32.34 | 2.7661 | 23.9 |
| 34.40 | 2.6047 | 5.4 |
| 34.62 | 2.5888 | 16.8 |
| 37.30 | 2.4088 | 7.5 |
| 37.50 | 2.3963 | 10.6 |
| 38.28 | 2.3492 | 5.0 |
| 38.96 | 2.3097 | 16.9 |
| 40.02 | 2.2510 | 6.4 |

Figure 4:
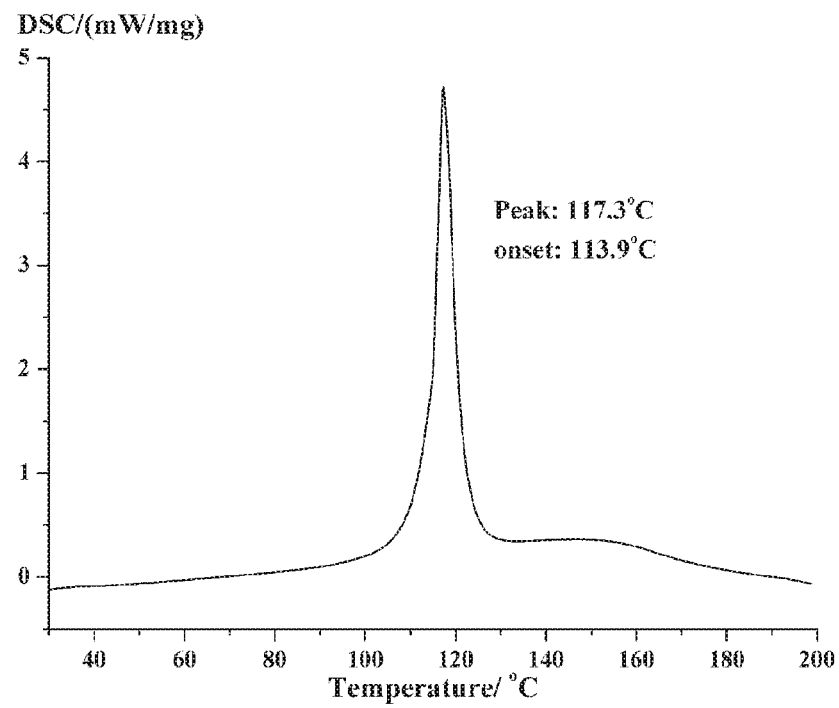
FIG. 4 is the differential scanning calorimetry (DSC) thermogram of the crystallized (S)-oxiracetam.

The differential scanning calorimetry (DSC) thermogram of the crystalline (S)-oxiracetam crystal form III is shown in FIG. 4, wherein the thermal transition temperature is 117.3° C.

Figure 5:
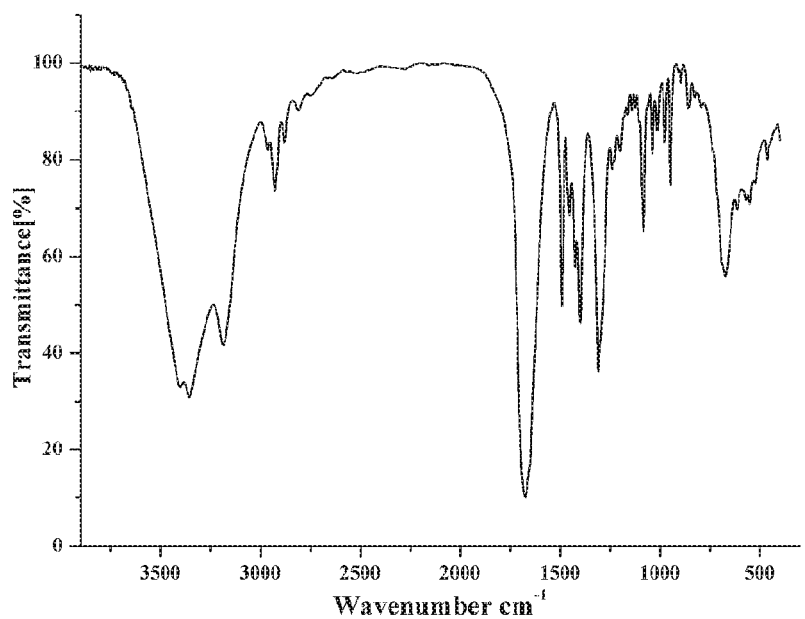
FIG. 5 is the infrared (IR) spectrum of the crystallized (S)-oxiracetam.

The infrared spectrum of the crystalline (S)-oxiracetam crystal form III is shown in FIG. 5, which exhibits absorption peaks at the following wave numbers: 3402, 3356, 3186, 2927, 2881, 2810, 1672, 1491, 1452, 1398, 1308, 1240, 1199, 1082, 1037, 1012, 947, 671, 613, and 461 cm$^{-1}$.

Example 3

20 mg (S)-oxiracetam is dissolved in 2 ml n-propanol solution, heated to 50° C., and filtered to form a supersaturated solution. The supersaturated solution is placed in a sealed environment at −17° C. for cooling crystallization for 3 hours, to give a colorless blocky crystal, identified as the crystal form III by using the method of Example 2.

Example 4

1 g (S)-oxiracetam is dissolved in 25 ml n-propanol solution, heated to 45° C., and filtered to form a supersaturated solution. The supersaturated solution is placed in a sealed environment at −18° C. for cooling crystallization for 36 hours, to give a colorless blocky crystal, identified as the crystal form III by using the method of Example 2.

Example 5

6 mg (S)-oxiracetam is dissolved in 1 ml isopropanol solution, heated to 40° C., and filtered to form a supersaturated solution. The supersaturated solution is placed in a sealed environment at −10° C. for cooling crystallization for 24 hours, to give a colorless blocky crystal, identified as the crystal form III by using the method of Example 2.

Example 6

60 mg (S)-oxiracetam is dissolved in 2 ml isopropanol solution, heated to 50° C., and filtered to form a supersaturated solution. The supersaturate solution is placed in a sealed environment at −19° C. for cooling crystallization for 36 hours, to give a colorless blocky crystal, identified as the crystal form III by using the method of Example 2.

Example 7

4 mg (S)-oxiracetam is dissolved in 2 ml sec-butanol solution, heated to 40° C., and filtered to form a supersaturated solution. The supersaturated solution is placed in a sealed environment at −17° C. for cooling crystallization for 24 hours, to give a colorless blocky crystal, identified as the crystal form III by using the method of Example 2.

Example 8

50 mg (S)-oxiracetam is dissolved in 2 ml sec-butanol solution, heated to 50° C., and filtered to form a supersaturated solution. The supersaturated solution is placed in a sealed environment at −19° C. for cooling crystallization for 36 hours, to give a colorless blocky crystal, identified as the crystal form III by using the method of Example 2.

Example 9

10 mg (S)-oxiracetam is dissolved in 1 ml water to form an aqueous solution, placed in a refrigerator of −19° C. to freeze for 3 hours, then taken out into a refrigerator of −80° C. to pre-freeze for 8 hours, and then placed in a vacuum freeze dryer for freeze drying for two days. The obtained crystal form is identified as the new crystal form III of (S)-oxiracetam by using the method of Example 2.

Example 10

20 mg (S)-oxiracetam is dissolved in 1 ml water to form an aqueous solution, placed in a refrigerator of −19° C. to freeze for 3 hours, then taken out into a refrigerator of −80° C. to pre-freeze for 8 hours, and then placed in a vacuum freeze dryer for freeze drying for two days. The obtained crystal form is identified as the new crystal form III of (S)-oxiracetam by using the method of Example 2.

Example 11

Taking preparing 1000 capsules of the crystal form III of (S)-oxiracetam for example, 200 mg crystal form III of (S)-oxiracetam prepared by using the method of Example 1, 80.8 mg lactose, 72 mg sodium carboxymethyl starch, 7.2 mg talcum powder and 10% polyvinyl pyrrolidone (PVP) in an appropriate amount, per capsule, are used. The specific preparation method is as follows: the raw materials are first sieved with an 80 mesh. The crystal form III of (S)-oxiracetam, lactose, and sodium carboxymethyl starch in the amount described above are mixed homogeneously to form a mixture. 10% PVP ethanol solution is added into the mixture to form a damp mass. The damp mass is processed through pellet fabrication, drying and granulation to form particles. The talcum powder in the amount described above is added into the particles and mixed homogeneously, then filled into the capsules.

Example 12

Take preparing 1000 tablets of the crystal form III of (S)-oxiracetam for example, 200 mg crystal form III of (S)-oxiracetam prepared by using the method of Example 1, 34 mg starch, 60 mg microcrystalline cellulose, 6 mg talcum powder and 2% hydroxypropyl methylcellulose (HPMC, K4M type) in an appropriate amount, per tablet, are used. The specific preparation method is as follows: the raw materials are first sieved with an 80 mesh. Then, the crystal form III of (S)-oxiracetam, starch, and microcrystalline cellulose in the amount described above are mixed homogeneously to form a mixture. 2% HPMC aqueous solution is added in an appropriate amount to the mixture to form a damp mass. The damp mass is processed through pellet fabrication, drying and granulation to form particles. The talcum powder is added into the particles in prescribed amount and mixed homogeneously, then compressed to form tablets.

Example 13

50 g crystal form III of (S)-oxiracetam prepared by using the method of Example 1, 50 g glucose, and 500 ml water for injection are dissolved in a diluted tank to form a solution. The temperature is controlled at 50° C. to 60° C., and the solution is agitated until the solvents were totally dissolved, then the temperature of the solution is decreased to 25° C. The solution is decolorized by adding charcoal to the above formulated solution, and then the charcoal is removed by filtering. The decolorized solution is added with phosphate buffer to adjust the pH value to 4.0, and then added with water for injection to 5000 ml, encapsulated and sterilized for 30 minutes at 105° C. to obtain an injection.

Example 14

Base on the existing LC-MS method for determination of (S)-oxiracetam in a biological sample, 6 healthy Beagle dogs are used in the experiment. They are weighted 8-10 kg, and divided into two groups of three. They are used to observe the bioavailability of the different crystal forms of (S)-oxiracetam after oral administration to the dogs. The pharmacokinetics of the crystal forms I and III of (S)-oxiracetam in the dogs are studied. And oxiracetam is used as reference preparation to evaluate whether the bioavailability of crystal forms I and III are equivalent. The bioequivalence is evaluated by calculating the pharmacokinetic parameters. Results: The main pharmacokinetic parameters of the crystal forms I and III of (S)-oxiracetam in the Beagle dogs are as follows: Tmax are (1.561±0.398) and (1.498±0.3988), Cmax are (198.076±80.462) and (186.205±50.321) mg/ml, respectively; $T_{1/2}$ are (0.915±0.125) and (0.909±0.112) h, respectively; and AUC0-∞ are (456.268±85.567) and (436.364±75.204) mg*h/ml, respectively. It can be seen that the bioavailability of the crystal form I and III of (S)-oxiracetam are exactly the same.

The invention claimed is:
1. A crystal form III of (S)-oxiracetam, having diffraction peaks appearing at the following 2θ diffraction angles: 14.44, 17.12, 18.88, 19.24, 20.66, 20.84, and 21.18°.
2. The crystal form III of (S)-oxiracetam according to claim 1, having diffraction peaks appearing at the following 2θ diffraction angles:
10.54, 13.70, 14.44, 15.60, 17.12, 18.88, 19.24, 20.66, 20.84, 21.18, 21.82, 22.94, 23.24, 24.88, 27.20, 27.48, 28.24, 30.46, 30.80, 31.52, 32.00, 32.34, 32.90, 33.20, 34.40, 34.62, 37.30, 37.50, 38.28, 38.96, and 40.02°.

3. The crystal form III of (S)-oxiracetam according to claim 1 having an X-ray powder diffraction data expressed in terms of d (Å)-values and relative intensity percentages I (%) as shown below:

| d value | I value | d value | I value |
| --- | --- | --- | --- |
| 8.3851 | 6.0 | 6.4588 | 8.5 |
| 6.1284 | 24.8 | 5.6744 | 10.0 |
| 5.1759 | 50.5 | 4.6969 | 100.0 |
| 4.6099 | 46.3 | 4.2960 | 34.2 |
| 4.2590 | 25.9 | 4.1914 | 71.1 |
| 4.0697 | 33.0 | 3.8735 | 33.8 |
| 3.8242 | 17.0 | 3.5761 | 67.5 |
| 3.2758 | 8.9 | 3.2429 | 7.9 |
| 3.1575 | 10.9 | 2.9324 | 19.8 |
| 2.9006 | 8.5 | 2.8362 | 23.2 |
| 2.7944 | 5.4 | 2.7661 | 23.9 |
| 2.6047 | 5.4 | 2.5888 | 16.8 |
| 2.4088 | 7.5 | 2.3963 | 10.6 |
| 2.3492 | 5.0 | 2.3097 | 16.9 |
| 2.2510 | 6.4. | | |

4. The crystal form III of (S)-oxiracetam according to claim 1, wherein the unit cell of the crystal form III of (S)-oxiracetam is orthorhombic, space group is $P4_1$, a=6.583 Å, b=6.583 Å, c=33.532(4) Å, α=90.000°, β=90.00°, γ=90.00°, and its cell volume V=1453.059(17) Å$^3$.

5. The crystal form III of (S)-oxiracetam according to claim 1, having absorption peaks appearing at the following wave numbers of produced infrared spectrum:
3402($cm^{-1}$), 3356($cm^{-1}$), 3186($cm^{-1}$), 2927($cm^{-1}$), 2881 ($cm^{-1}$), 2810($cm^{-1}$), 1672($cm^{-1}$), 1491($cm^{-1}$), 1452 ($cm^{-1}$), 1398($cm^{-1}$), 1308($cm^{-1}$), 1240($cm^{-1}$), 1199 ($cm^{-1}$), 1082($cm^{-1}$), 1037($cm^{-1}$), 1012($cm^{-1}$), 947 ($cm^{-1}$), 671($cm^{-1}$), 613($cm^{-1}$), and 461($cm^{-1}$).

6. The crystal form III of (S)-oxiracetam according to claim 1, having a thermal transition temperature of 117.3° C.

7. The preparation method of the crystal form III of (S)-oxiracetam according to claim 1, comprising the following steps:
dissolving (S)-oxiracetam in isopropanol solvent at 5 mg/ml-50 mg/ml, stirring, heating to 30° C. to 100° C. to dissolve, filtering to form a supersaturated solution;
placing the supersaturated solution obtained in step (1) in a sealed low temperature environment at −10° C. to −19° C. for cooling crystallization, to give colorless blocky crystal, which is the new crystal form III of (S)-oxiracetam.

8. The preparation method of crystal form III of (S)-oxiracetam according to claim 7, wherein the heating temperature to dissolve is arranged at 40° C. to 50° C.

9. The preparation method of crystal form III of (S)-oxiracetam according to claim 7, wherein the low temperature environment is arranged at −17° C. to −19° C.

10. The preparation method of crystal form III of (S)-oxiracetam according to claim 9, wherein:
dissolving (S)-oxiracetam in isopropanol solvent at 5 mg/ml-50 mg/ml, stirring constantly, heating to 40° C. to 50° C. to dissolve, filtering to form a supersaturated solution;
placing the supersaturated solution in a sealed environment at −17° C. to −19° C. for cooling crystallization for 24-36 hours, to give a colorless blocky crystal, of a crystal form III of (S:)-oxiracetam.

11. A pharmaceutical composition, comprising the crystal form III of (S)-oxiracetam of claim 1, in pharmaceutically acceptable excipients.

12. The crystal form III of (S)-oxiracetam according to claim 2, having an X-ray powder diffraction data expressed in terms of d (Å)-values and relative intensity percentages I (%) as shown below:

| d value | I value | d value | I value |
| --- | --- | --- | --- |
| 8.3851 | 6.0 | 6.4588 | 8.5 |
| 6.1284 | 24.8 | 5.6744 | 10.0 |
| 5.1759 | 50.5 | 4.6969 | 100.0 |
| 4.6099 | 46.3 | 4.2960 | 34.2 |
| 4.2590 | 25.9 | 4.1914 | 71.1 |
| 4.0697 | 33.0 | 3.8735 | 33.8 |
| 3.8242 | 17.0 | 3.5761 | 67.5 |
| 3.2758 | 8.9 | 3.2429 | 7.9 |
| 3.1575 | 10.9 | 2.9324 | 19.8 |
| 2.9006 | 8.5 | 2.8362 | 23.2 |
| 2.7944 | 5.4 | 2.7661 | 23.9 |
| 2.6047 | 5.4 | 2.5888 | 16.8 |
| 2.4088 | 7.5 | 2.3963 | 10.6 |
| 2.3492 | 5.0 | 2.3097 | 16.9 |
| 2.2510 | 6.4. | | |

13. The crystal form III of (S)-oxiracetam according to claim 2, having an absorption peaks appearing at the following wave numbers of produced infrared spectrum:
3402($cm^{-1}$), 3356($cm^{-1}$), 3186($cm^{-1}$), 2927($cm^{-1}$), 2881 ($cm^{-1}$), 2810($cm^{-1}$), 1672($cm^{-1}$), 1491($cm^{-1}$), 1452 ($cm^{-1}$), 1398($cm^{-1}$), 1308($cm^{-1}$), 1240($cm^{-1}$), 1199 ($cm^{-1}$), 1082($cm^{-1}$), 1037($cm^{-1}$), 1012($cm^{-1}$), 947 ($cm^{-1}$), 671($cm^{-1}$), 613($cm^{-1}$), and 461($cm^{-}$).

14. The crystal form III of (S)-oxiracetam according to claim 4, having an absorption peaks appearing at the following wave numbers of produced infrared spectrum:
3402($cm^{-1}$), 3356($cm^{-1}$), 3186($cm^{-1}$), 2927($cm^{-1}$), 2881 ($cm^{-1}$), 2810($cm^{-1}$), 1672($cm^{-1}$), 1491($cm^{-1}$), 1452 ($cm^{-1}$), 1398($cm^{-1}$), 1308($cm^{-1}$), 1240($cm^{-1}$), 1199 ($cm^{-1}$), 1082($cm^{-1}$), 1037($cm^{-1}$), 1012($cm^{-1}$), 947 ($cm^{-1}$), 671($cm^{-1}$), 613($cm^{-1}$), and 461($cm^{-1}$).

15. The crystal form III of (S)-oxiracetam according to claim 2, having a thermal transition temperature of 117.3° C.

16. The pharmaceutical composition according to claim 11, wherein the crystal form III of (S)-oxiracetam has diffraction peaks appearing at the following 2θ diffraction angles: 10.54, 13.70, 14.44, 15.60, 17.12, 18.88, 19.24, 20.66, 20.84, 21.18, 21.82, 22.94, 23.24, 24.88, 27.20, 27.48, 28.24, 30.46, 30.80, 31.52, 32.00, 32.34, 32.90, 33.20, 34.40, 34.62, 37.30, 37.50, 38.28, 38.96, and 40.02°.

17. The pharmaceutical composition according to claim 11, wherein the crystal form III of (S)-oxiracetam has an X-ray powder diffraction data expressed in terms of d (Å)-values and relative intensity percentages I (%) as shown below:

| d value | I value | d value | I value |
| --- | --- | --- | --- |
| 8.3851 | 6.0 | 6.4588 | 8.5 |
| 6.1284 | 24.8 | 5.6744 | 10.0 |
| 5.1759 | 50.5 | 4.6969 | 100.0 |
| 4.6099 | 46.3 | 4.2960 | 34.2 |
| 4.2590 | 25.9 | 4.1914 | 71.1 |
| 4.0697 | 33.0 | 3.8735 | 33.8 |
| 3.8242 | 17.0 | 3.5761 | 67.5 |
| 3.2758 | 8.9 | 3.2429 | 7.9 |
| 3.1575 | 10.9 | 2.93.24 | 19.8 |
| 2.9006 | 8.5 | 2.8362 | 23.2 |
| 2.7944 | 5.4 | 2.7661 | 23.9 |
| 2.6047 | 5.4 | 2.5888 | 16.8 |
| 2.4088 | 7.5 | 2.3963 | 10.6 |
| 2.3492 | 5.0 | 2.3097 | 16.9 |
| 2.2510 | 6.4. | | |

18. The pharmaceutical composition according to claim 11, wherein the unit cell of the crystal form III of (S)-oxiracetam is orthorhombic, space group is $P4_1$, a=6.583 Å, b=6.583 Å, c=33.532(4) Å, $\alpha$=90.00°, $\beta$=90.00°, $\gamma$=90.00°, and its cell volume V=1453.059(17) Å$^3$.

19. The pharmaceutical composition according to claim 11, wherein the crystal form III of (S)-oxiracetam has absorption peaks appearing at the following wave numbers of produced infrared spectrum:

3402(cm$^{-1}$), 3356(cm$^{-1}$), 3186(cm$^{-1}$), 2927(cm$^{-1}$), 2881 (cm$^{-1}$), 2810(cm$^{-1}$), 1672(cm$^{-1}$), 1491(cm$^{-1}$), 1452 (cm$^{-1}$), 1398(cm$^{-1}$), 1308(cm$^{-1}$), 240(cm$^{-1}$), 1199 (cm$^{-1}$), 1082(cm$^{-1}$), 1037(cm$^{-1}$), 1012(cm$^{-1}$), 947 (cm$^{-1}$), 671(cm$^{-1}$), 613(cm$^{-1}$), and 461(cm$^{-1}$).

20. The pharmaceutical composition according to claim 11, wherein the crystal form III of (S)-oxiracetam has a thermal transition temperature of 117.3° C.

\* \* \* \* \*